United States Patent [19]

Yamada

[11] Patent Number: 4,731,065
[45] Date of Patent: Mar. 15, 1988

[54] SANITARY NAPKIN

[76] Inventor: Yutaka Yamada, 5-15-9, Minamikarasuyama, Setagaya-ku, Tokyo, Japan

[21] Appl. No.: 788,515

[22] Filed: Oct. 18, 1985

Related U.S. Application Data

[63] Continuation of Ser. No. 535,272, Sep. 23, 1983, abandoned.

[30] Foreign Application Priority Data

Jan. 24, 1983 [JP] Japan .................. 58-8615[U]
Jan. 24, 1983 [JP] Japan .................. 58-8616[U]
Apr. 15, 1983 [JP] Japan .................. 58-57142[U]
Apr. 15, 1983 [JP] Japan .................. 58-57143[U]
Jun. 30, 1983 [JP] Japan .................. 58-101365[U]

[51] Int. Cl.$^4$ ............................. A61F 5/44
[52] U.S. Cl. ............................. 604/355; 604/378
[58] Field of Search .......... 604/355, 366, 370, 378, 604/379, 380, 389, 390, 385.1

[56] References Cited

U.S. PATENT DOCUMENTS

| | | | |
|---|---|---|---|
| 3,046,986 | 7/1962 | Harwood | 604/378 |
| 3,364,931 | 1/1968 | Hirsch | 604/366 |
| 3,424,160 | 1/1969 | Koornwinder et al. | 604/348 |
| 3,441,023 | 4/1969 | Rijssenbeek | 604/378 |
| 4,031,897 | 6/1977 | Graetz | 604/347 |
| 4,046,147 | 9/1977 | Berg | 604/390 |
| 4,285,342 | 8/1981 | Mesek | 604/389 |
| 4,333,462 | 6/1982 | Holtman et al. | 604/378 |

Primary Examiner—John D. Yasko
Attorney, Agent, or Firm—Watson, Cole, Grindle & Watson

[57] ABSTRACT

A sanitary napkin for receiving excretions includes a flat, elongate water absorbing napkin body. That part of the napkin body which contacts the excretory organs is formed with a recess which serves as an excretion receiving space to enhance the absorptivity and to increase the capacity of the napkin. The napkin can be conveniently used to receive menstrual blood, urine or feces.

8 Claims, 23 Drawing Figures

SANITARY NAPKIN

This application is a continuation, of application Ser. No. 535,272, filed Sept. 23, 1983, now abandoned.

BACKGROUND OF THE INVENTION

1. Field of the Invention

This invention relates generally to a napkin for receiving excretions such as menstrual blood, urine or feces discharged from a human body, and more particularly to a compact water-absorbing napkin which can be utilized by females to receive menstrual blood, or which can be utilized to receive feces or urine discharged from babies, infants, or sick or wounded persons unable to walk by themselves. The napkin can be used to receive feces or it urine in case of urgency, or can be used daily to receive feces or urine of old persons having impaired excretory control functions.

2. Description of the Prior Art

Figure 23:
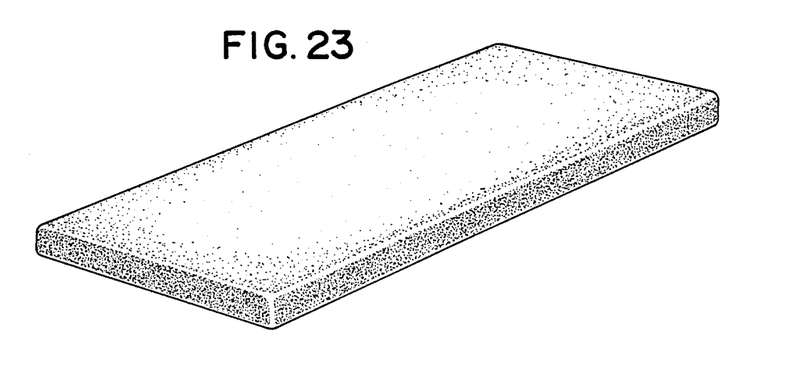
FIG. 23 is a perspective view illustrating a prior art excretion-receiving napkin.

Commercially available prior art water-absorbing napkins for receiving menstrual blood, feces or urine typically have a flat, elongate form, as shown in FIG. 23. The part of the napkin which is to be brought into contact with the excretory organs extends coextensively along the wide surface of the napkin.

Thus, in a sanitary napkin, for example, the even, wide napkin surface flatly contacts the excretory organs and the surrounding body area without providing any gap or recess to absorb menstrual blood. However, the blood tends to flow under capillary action between the even, flat surface of the napkin and the excretory organs to leak laterally therebetween. This defect results from the contact of the excretory organs with the napkin along the same plane as the wide napkin surface. When a relatively large amount of menstrual blood must be absorbed or when a female wearing a sanitary napkin moves to cause the napkin to be slipped off, the problem of blood leakage becomes particularly serious. In such a case, the user feels uncomfortable and the surrounding lingerie may be stained by blood.

Napkins can also be used by females for absorbing urine. However, in this case since only a limited spot-like area of a prior art napkin is brought into contact with the excretory organs, the absorptivity of this area is necessarily lower than that required to absorb all the urine discharged. As a result, the urine overflows the absorbing area, so that one may feel uneasy having wet excretory organs and a wet surrounding body area, even if part of the urine has been absorbed.

In a typical prior art napkin for receiving feces, there is typically no gap provided between the excretory organs and the area around them and the napkin, thereby causing feces to readily extend over and cling to the excretory organs. It is troublesome to subsequently cleanse such condition.

SUMMARY OF THE INVENTION

In accordance with one feature of this invention, that part of a flat and elongate napkin body which is brought into contact with the excretory organs is formed with a recess to define a space in which excretions are received. The napkin may serve as a sanitary napkin or to receive feces or urine of male as well as female users.

More particularly, if the napkin is formed as a sanitary napkin, the napkin body is formed with an elongate recess of a relatively small depth. As a result, the wide surface of the napkin will have a concave vertical section as well as a convex cross section when the napkin contacts the excretory organs. Simultaneously, the inner circumferential surface of the recess which is formed as an annular ridge contacts the area around the excretory organs to surround and support them. Consequently, the napkin will not slip off the body of the user.

An annular space which is defined between the napkin body and the excretory organs, at least along the annular ridge, serves to prevent the flow of menstrual blood under capillary action which often occurs in conventional sanitary napkins and to permit the blood to be absorbed within the recess. Furthermore, since the inner circumferential surface of the recess also serves as an absorbing surface which increases the absorptivity of the napkin to a degree at least twice that of conventional napkins, lateral leakage of menstrual blood can be completely avoided. Therefore, one may freely move about while using the napkin. Moreover, the lingerie of the user will no longer be stained by leaking blood.

In a napkin for absorbing urine according to this invention, the napkin body has a circular recess for males or an elongate elliptical recess for females, each recess having a relatively large depth to receive the excretory organs. The inner circumferential surface of the recess is formed with an annular ridge to contact the area around the excretory organs so as to surround, hold and support them. As a result, the napkin will not slip off the body, thereby avoiding the scattering or leakage of urine. Furthermore, since the inner circumferential surface of the deep recess serves as an absorbing surface to increase the absorptivity of the napkin to a degree at least twice that of prior art napkins, the undesirable problem of overflow of urine from the recess can be eliminated. Therefore, discomfort encountered during discharge while using conventional napkins can be completely avoided, so that the napkin can be worn comfortably.

In a napkin for receiving feces, the napkin body is formed with an elongate and deep recess to receive feces. The inner circumferential surface of the recess is formed with an annular ridge to prevent the feces from moving out of the recess and to securely hold the feces therein. As a result, the excretory organs and the area around them are no longer stained by feces. This enhances comfort and facilitates cleansing after discharge.

According to another aspect of this invention, the napkin body may be formed in such a manner that the entire surface of the napkin body, except for the recess portion of the recess is covered with an unwoven membrane which is water insoluble. Such a napkin is suitable for use as a sanitary napkin, a napkin for receiving feces or one which is used daily to receive excretions from elderly people. Alternatively, the entire napkin surface except for the recess or only the rear napkin surface may be covered with a waterproof film. Such a structure is suitable for a napkin for absorbing urine.

The recess of the napkin may be formed by cutting off a corresponding napkin portion or by folding napkin strips inward to leave a recess. The recess may also be covered with a water-permeable film which is water insoluble. The first type of napkin is suitable for receiving menstrual blood and feces as well as for daily use as a napkin for receiving excretions of elderly people. In the second type of napkin with folding strips, a passage space is formed about the folding strip which communicates with the recess. Consequently, urine is continuously absorbed by the absorbing surface which is enlarged by adding this passage space while flowing from the recess into the passage space. Thus, such a napkin can be conveniently used to absorb urine. In a third type of napkin, a water-permeable film contacts the excretory organs so as to allow urine to flow into the recess, while the scattering and splash of urine can be avoided. Furthermore, urine which trickles down immediately before it has been completely discharged and urine remaining on the excretory organs can be absorbed as though it were wiped off. Thus, such a napkin can be conveniently used by females to absorb urine.

The napkin in accordance with this invention can be fixed by means of a special supporter or by directly placing it on a diaper cover or underwear.

This invention further includes an embodiment in which the width of the recess is increased from the inlet toward the bottom thereof. Such a napkin having a high absorption efficiency for menstrual blood and urine is preferably used as a sanitary napkin or a napkin for receiving urine. It can be also effectively used to receive feces, since the receiving space is enlarged.

BRIEF DESCRIPTION OF THE DRAWINGS

Various other objects, features and attendant advantages of the present invention will be more fully appreciated as the same becomes better understood from the following detailed description when considered in connection with the accompanying drawings, in which like reference characters designate like or corresponding parts through the several views and wherein.

DETAILED DESCRIPTION OF THE PREFERRED EMBODIMENTS

Figure 1:
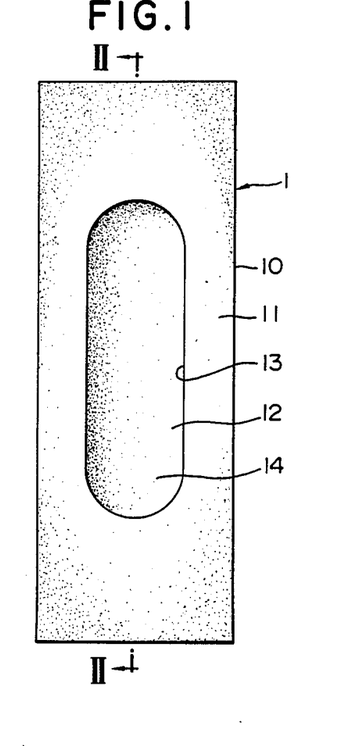
FIGS. 1 through 4 show a sanitary napkin in accordance with a first embodiment, FIG. 1 showing a front view of the napkin, FIG. 2 showing a vertical sectional view taken along line II—II of FIG. 1, FIG. 3 showing a transverse sectional view illustrating the napkin in use, and FIG. 4 showing a vertical sectional view illustrating the napkin in use.

FIGS. 1 through 4 depict a sanitary napkin 1 in accordance with a first embodiment of this invention which includes a napkin body 10 having a membranous bag element 11 and an absorbent element 12. The bag element 11 is made of a paper material such as synthetic fiber paper which is water insoluble, but through which water can permeate. Bag element 11 is shaped into the form of an elongate bag having flat side surfaces. The front part of the bag element 11 which is to be brought into contact with the excretory organs, that is, the wider surface of the bag element, is provided with an elongate opening 13. The absorbent element 12 is accommodated within the bag element 11. The bag element 11 may have an elongate rectangular form as shown in FIG. 1, or a reversed trapezoidal or elongate elliptical form, or any other suitable form, when seen from the front side.

Figure 2:
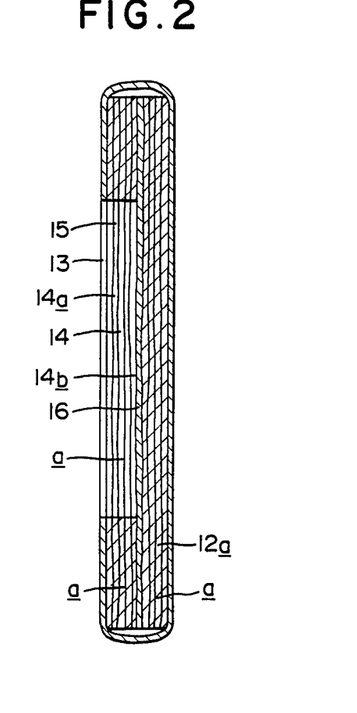
Figures 3, 4:
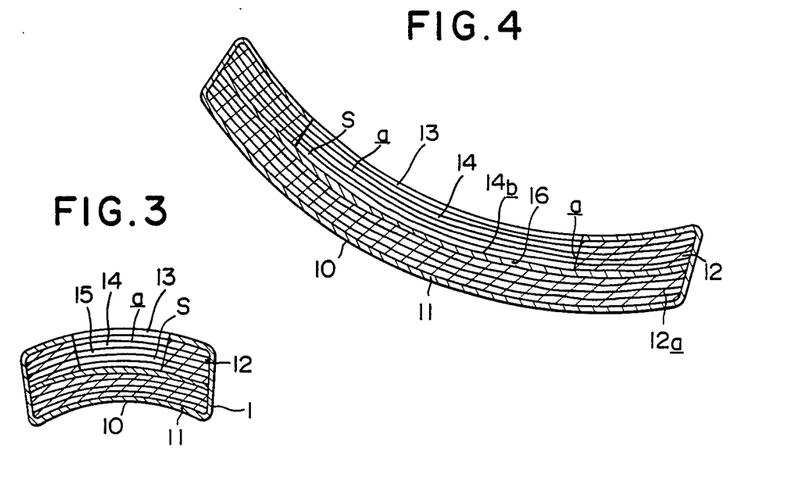

The absorbent element 12 is made of a material which is excellent in flexibility and absorptivity. For example, pulp material, synthetic fibers mixed with pulp fibers, and a highly absorbent material such as SMC may be used. The absorbent element 12 is formed with a flat lamination of many water-absorbing paper layers 12a as shown in FIG. 2 and has formed therein a recess 14 as shown in FIG. 3 of the same front side form as that of the opening 13 and having an appropriate depth with respect to the outer surface of the napkin bordering the opening 13.

The inner circumferential surface 14a of the recess 14 is formed as an annular ridge 15 which surrounds the excretory organs when the napkin is brought into contact with them. In this case, an annular space S as shown in FIGS. 3 and 4 is ensured between the inner circumferential surface 14a and the excretory organs. The bottom surface 14b of the recess 14 is made of water-permeable paper 16 such as synthetic fiber paper which is water insoluble. Therefore, when the bottom surface 14b is in contact with the excretory organs, it will not cling thereto so that the napkin can be comfortably worn.

The lamination density of the respective water-absorbing paper layers 12a is selected so that the water-absorbing paper layers can be overlapped with each other without significant external pressure being exerted thereto so that the necessary flexibility of the entire napkin 1 will not decreased. An almost infinite number of capillaries a are formed between the adjacent water-absorbing paper layers 12a. These capillaries a open into and communicate with the inner circumferential surface 14a of the recess 14 so that menstrual blood can be abosrbed under capillary action, not only by the bottom surface 14b, but also by the inner circumferential surface 14a.

Each of the water-absorbing paper layers 12a of the absorbent element 12 is made of a water-absorbing paper which is rimpled in one direction along the longitudinal direction of the napkin. In this manner the capillaries a formed along an almost infinite number of rimples communicate with the recess 14 from above and from below, whereby the blood may smoothly and readily flow downward due to its own weight. Furthermore, the width of the napkin 1 can be reduced to a greater extent during use so that it can be securely held on the excretory organs and appropriately deformed.

The napkin thus formed provides the following advantages in practical use. Since the bag element 11 forming the outer surface of the napkin 1 is made of water-permeable paper which is water insoluble and agreeable to the touch, the napkin 1 can be comfortably worn. The small spaces between the respective water-absorbing paper layers 12a laminated in the recess 14 serve as capillaries a which open into and communicate with the inner circumferential surface 14a of the recess 14. Consequently, the absorptivity of the paper itself is combined with the absorptivity provided by the respective capillaries to significantly increase the absorptive power of the napkin assembly. Since the absorbent element 12 is formed with a flat lamination including a number of water absorbing paper layers 12a, element 12 is excellent in flexibility and can be appropriately deformed. Therefore, element 12 feels soft and smooth when brought into contact with the body. Further, even after the napkin absorbs the excretion, i.e., blood, it still remains flexible and soft. In summary, the napkin does not make the user feel uneasy about the foreign matter, that is, the napkin, which is in contact with the body.

Figure 5:
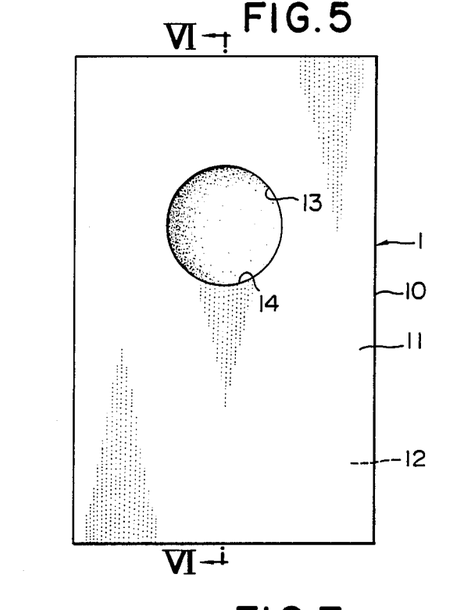
FIGS. 5 and 6 show a napkin for absorbing urine in accordance with a second embodiment which can be used by males, FIG. 5 showing a front view of the napkin, and FIG. 6 showing a vertical sectional view taken along line VI—VI of FIG. 5.
Figure 6:
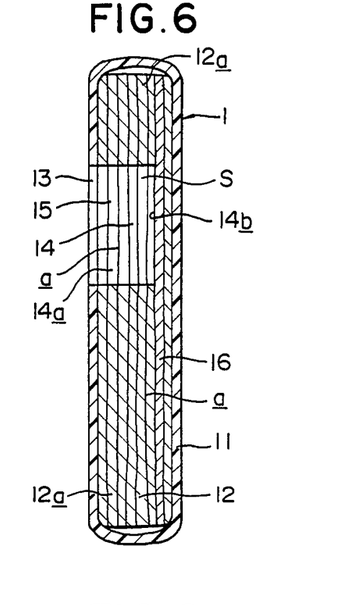

As depicted in FIGS. 5 and 6, a napkin 1 for absorbing urine in accordance with a second embodiment of this invention can be used by males and includes a napkin body 10 including a membranous bag element 11 and an absorbent element 12. The bag element 11, on both sides, is made of a waterproof synthetic fiber resin film or the like and shaped into the form of an elongate bag having flat side surfaces. An opening 13 having an appropriate form such as a circular opening as illustrated in FIG. 5 is provided at the center of the upper half portion of the bag element 11 in the front surface thereof. The absorbent element 12 is accommodated within the bag element 11. The bag element 11 may have an elongate rectangular form as shown in FIG. 5, or a reversed trapezoidal or elongate elliptical form, or any other suitable form, when seen from the front side.

The absorbent element 12 has the same features and functions in substantially the same manner as element 12 discussed above in connection with the first embodiment. In the second embodiment, it is desirable to form a deep recess 14 in order to increase the area in which urine can be absorbed.

The lamination density of water-absorbing paper layers 12a is selected as set forth above in the discussion of the first embodiment. Capillaries a open into and communicate with the inner circumferential surface 14a of the recess 14, so that urine can be absorbed under capillary action not only by the bottom surface 14b, but also by the inner circumferential surface 14a. Each of the water-absorbing paper layers 12a of the absorbent element 12 is made as indicated above.

The napkin thus formed in accordance with the second embodiment provides the following advantages in practical use. Since the small spaces between the respective water-absorbing paper layers 12a laminated in the recess 14 serve as capillaries a which open into and communicate with the inner circumferential surface 14a of the recess 14, the absorptivity of the paper itself is combined with the absorptivity provided by the respective capillaries to significantly increase the absorptive power of the napkin assembly. Since the absorbent element 12 is formed with a flat lamination of a number of water-absorbing paper layers 12a, it is excellent in flexibilty and can be appropriately deformed. Therefore, it feels soft and smooth when brought into contact with the body. Further, even afer the napkin 1 absorbs urine, it still remains flexible and soft. In summary, the napkin does not make the user feel uneasy about the foreign matter, that is, the napkin, which is in contact with the body. Since the bottom surface 14b of the recess 14 is made of water-permeable paper which is water insoluble, it is agreeable to the touch and does not cling to the body.

Figure 7:
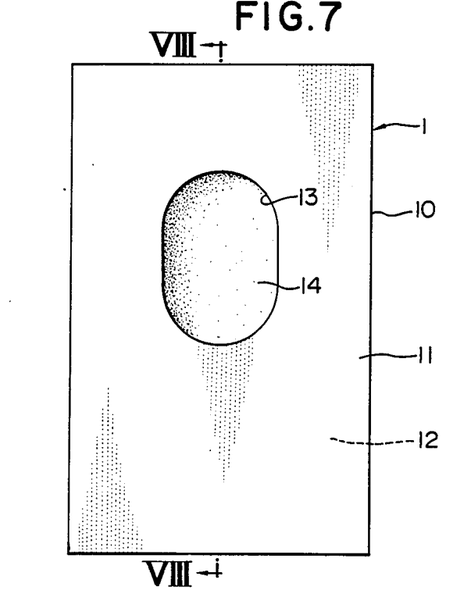
FIGS. 7 and 8 show a napkin for absorbing urine in accordance with a third embodiment which can be used by females, FIG. 7 showing a front view of the napkin, and FIG. 8 showing a vertical sectional view taken along line VIII—VIII of FIG. 7.
Figure 8:
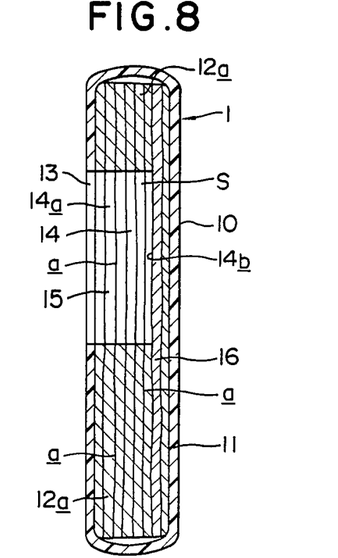

As shown in FIGS. 7 and 8, a napkin 1 for absorbing urine in accordance with a third embodiment of this invention can be used by females and includes a napkin body 10 including a membranous bag element 11 and an absorbent element 12. The bag element 11 is made of waterproof synthetic resin film or the like and shaped into the form of an elongate bag having flat side surfaces. An opening 13 having an appropriate form is provided at the center of the upper half portion of the bag element in the front surface thereof. The opening 13 is elongate in principle. An elliptical opening is shown in FIG. 7. The absorbent element 12 is accommodated within the bag element 11. The bag element 11 may have an elongate rectangular form as shown in FIG. 7, or a reversed trapezoidal or elongate elliptical form, or any other suitable form, when seen from the front side.

The absorbent element 12 of the third embodiment is made as set forth above and functions in a similar manner. It is desirable to form a deep recess 14 in order to increase the area in which urine can be absorbed. Capillaries a open into and communicate with the inner circumferential surface 14a of the recess 14, so that urine can be absorbed under capillary action not only by the bottom surface 14b, but also by the inner circumferential surface 14a. The capillaries a formed along an almost infinite number of rimples communicate with the recess 14 from above and from below, whereby the urine may smoothly and readily flow downward due to its own weight.

The napkin thus formed in accordance with the third embodiment provides the same advantages in practical use as those advantages enumerated above in connection with the second embodiment of the invention.

Figure 9:
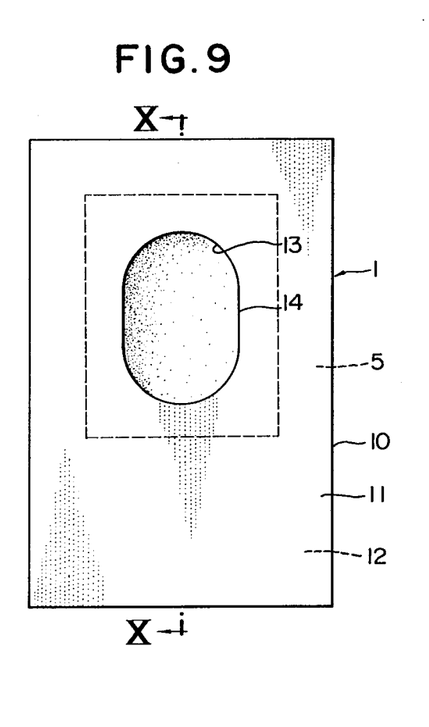
FIGS. 9 and 10 also show a napkin for absorbing urine in accordance with a fourth embodiment which can be used by females, FIG. 9 showing a front view of the napkin, and FIG. 10 showing a vertical sectional view taken along line X—X of FIG. 9.
Figure 10:
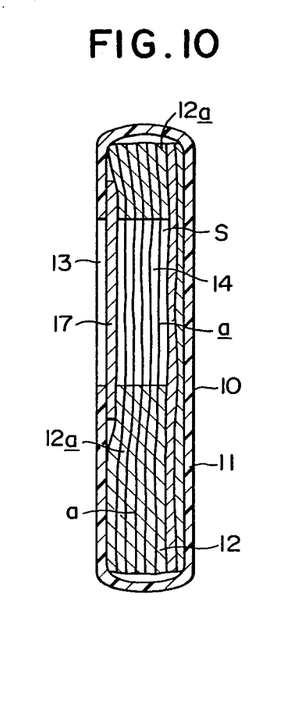

As depicted in FIGS. 9 and 10, a napkin 1 for absorbing urine in accordance with a fourth embodiment of this invention can be used by females and includes a napkin body 10 including a membranous bag element 11 and an absorbent element 12. The bag element is made of a waterproof synthetic resin film or the like and shaped into the form of an elongate bag having flat side surfaces. An opening 13 having an appropriate form is provided at the center of the upper half part of the bag element in the front surface thereof. The opening 13 is elongate in principle. An elliptical opening is shown in FIG. 9. The absorbent element 12 is accommodated within the bag element 11. A water-permeable, water-insoluble membrane 17 is provided in the position corresponding to the opening 13 so as to block the inlet to recess 14 of the absorbent element 12. The bag element 11 may have an elongate rectangular form as shown in FIG. 9 or a reversed trapezoidal or elongate elliptical form, or any other suitable form, when seen from the front side.

The absorbent element 12 is made as noted above. Urine can be absorbed under capillary action not only by the bottom surface 14b of the recess 14, but also by the inner circumferential surface 14a. The water-permeable membrane 17 is made of highly water-permeable water-insoluble synthetic fiber paper and interposed between the opening 13 and the recess 14 as shown in FIG. 10. It is desirable that the membrane 17 does not prevent the urine from flowing from the opening 13 into the recess 14 and can absorb with the help of its own absorptivity the urine remaining on the side of the opening 13 adjacent the body of the user. In addition, the water-permeable membrane 17 preferably feels soft and comfortable.

The napkin thus formed in accordance with the fourth embodiment provides the following advantages in practical use. The water-permeable membrane 17 provided in the position corresponding to the opening 13 is brought into contact with the excretory organs and does not prevent the urine from flowing into the recess 14. Moreover, scattering and leakage of the urine are avoided. The urine which trickles down immediately before the urine has been completely discharged as well as the urine remaining on the body can be absorbed as if it were wiped off.

Since the small spaces between the respective water absorbing paper layers 12a laminated in the recess 14 serve as capillaries a which open into and communicate with the inner circumferential surface 14a of the recess 14, the absorptivity of the paper itself is combined with the absorptivity provided by the respective capillaries to significantly increase the absorptive power of the napkin assembly.

Since the absorbent element 12 is formed with a flat lamination of a number of water-absorbing paper layers 12a, it is excellent in flexibility and can be appropriately deformed. Therefore, it feels soft and smooth when brought into contact with the body. Further, even after the napkin absorbs urine, it still remains flexible and soft. In summary, the napkin does not make the user feel uneasy about the foreign matter, that is, the napkin, which is in contact with the body.

Figure 11:
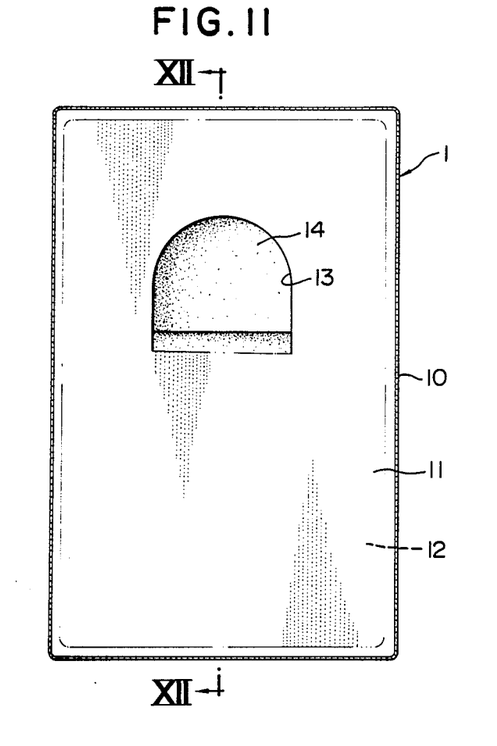
FIGS. 11 through 14 show a napkin for absorbing urine in accordance with a fifth embodiment which can be used by males, FIG. 11 showing a front view of the napkin, FIG. 12 showing a vertical sectional view taken along line XII—XII of FIG. 11, FIG. 13 showing a transverse sectional view taken along line XIII—XIII of FIG. 12, and FIG. 14 showing a front view of the napkin before a recess has been formed.
Figure 12:
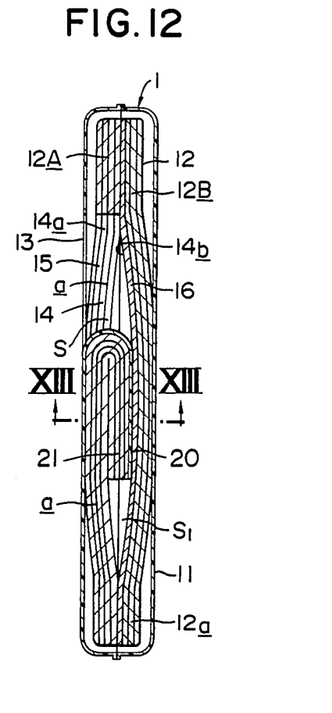
Figure 13:
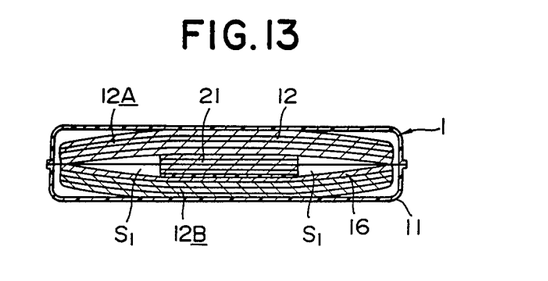
Figure 14:
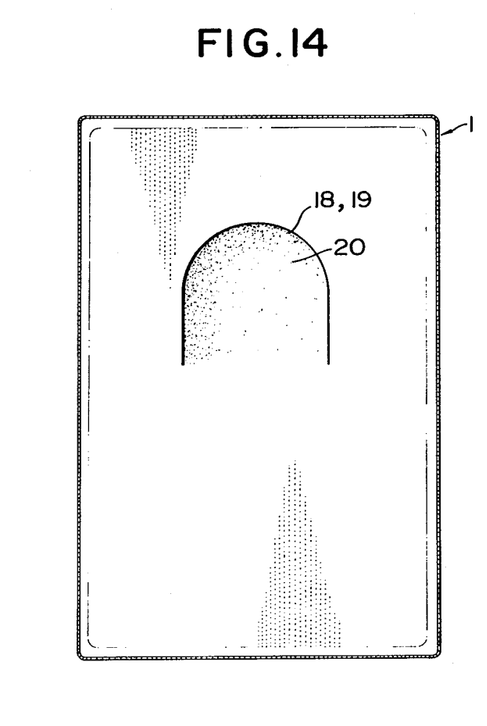

As shown in FIGS. 11 through 14, a napkin 1 for abosrbing urine in accordance with a fifth embodiment of this invention can be used by males and includes a napkin body 10 including a membranous bag element 11 and an absorbent element 12. The bag element 11 is made of waterproof synthetic resin film or the like and shaped into the form of an elongate bag having flat side surfaces. The absorbent element 12 is accommodated within the bag element 11. Breaking or shear lines 18 and 19 each having an arcuate reversed U shape are formed at the center of the upper half portion of the napkin body 10 in the front surface thereof. Folding strips 20 and 21 of the bag element 11 and the absorbent element 12 are respectively folded inwardly from the breaking lines 18 and 19 to leave or define a recess 14. The bag element 11 may have an elongate rectangular form as shown in FIG. 11, or a reversed trapezoidal or elongate elliptical form, or any other suitable form, when seen from the front side.

The absorbent element 12 is made with the same construction as indicated above except element 12 is formed with a flat lamination of many water-absorbing paper layers 12a to form a double-layer structure including an outer layer part 12A and a rear layer part 12B. The folding strip 21 folded between these outer and rear layers parts 12A and 12B forms a space between both layer parts excluding the folded portion. In this manner, a generally C-shape passage space S1 is formed which communicates with the recess 14. It can be seen that this passage space S1 has a generally triangular-shaped cross section.

It is desirable to form a deep recess 14 in order to increase the area in which urine can be absorbed. In addition, the recess 14 has the same width both in the vertical direction and the horizontal direction so that the napkin may be readily and securely held on the excretory organs. The napkin thus formed in accordance with the fifth embodiment provides the same advantages in practical use as those advantages enumerated above in connection with the second embodiment of the invention.

Figure 15:
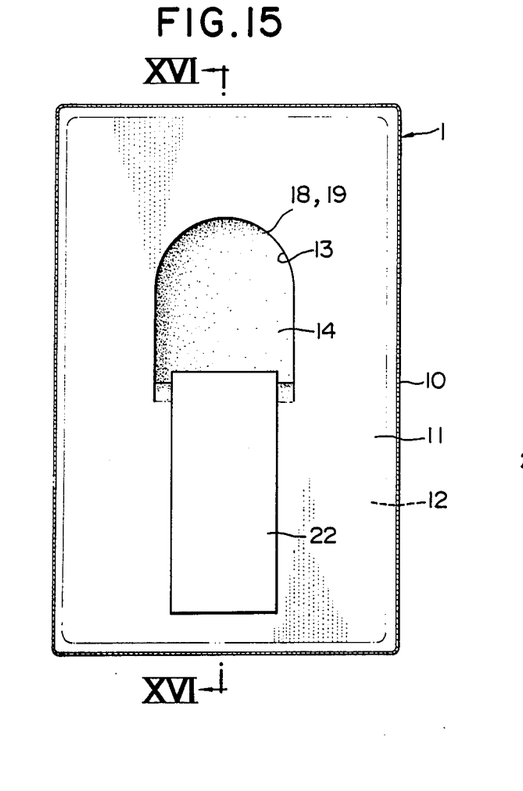
FIGS. 15 through 18 show a napkin for absorbing urine in accordance with a sixth embodiment which can be used by females, FIG. 15 showing a front view of the napkin, FIG. 16 showing a vertical sectional view taken along line XVI—XVI of FIG. 15, FIG. 17 showing a transverse sectional view taken along line XVII—XVII of FIG. 16, and FIG. 18 showing a front view of the napkin before a recess has been formed.
Figure 16:
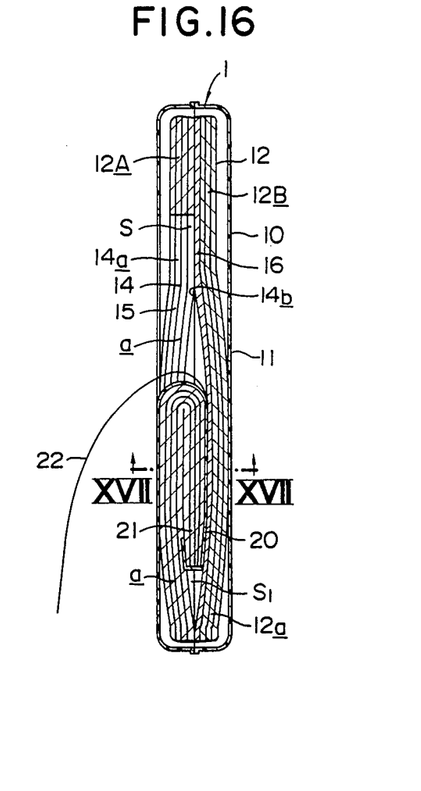
Figure 17:
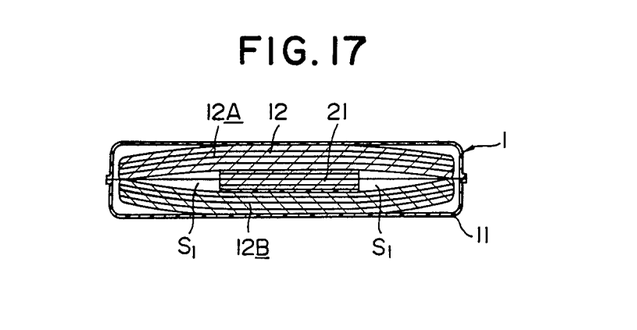
Figure 18:
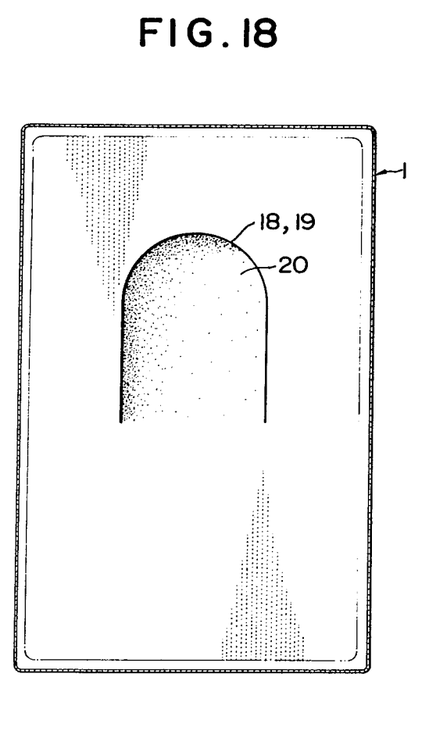

As shown in FIGS. 15 through 18, a napkin 1 for absorbing urine in accordance with a sixth embodiment of this invention can be used by females and includes a napkin body 10 including membranous bag element 11 and an absorbent element 12. The bag element 11 is made of a waterproof synthetic resin film or the like and shaped into the form of an elongate bag having flat side surfaces. The absorbent element 12 is accommodated within the bag element 11. Breaking lines 18 and 19 each having an arcuate reversed U shape are formed at the center of the upper half portion of the napkin body 10 in the front surface thereof. Folding strips 20 and 21 of the bag element 11 and the absorbent element 12 are respectively folded inwardly from the breaking lines 18 and 19 to leave an elongate recess 14. The bag element 11 may have an elongate rectangular form as shown in FIG. 15, or a reversed trapezoidal or elongate elliptical form, or any other suitable form, when seen from the front side.

The absorbent element 12 is made of a material which is excellent in flexibility and absorptivity. Pulp material, synthetic fibers mixed with pulp fibers, and a highly absorbent material such as SMC may be used, for example. The absorbent element 12 is formed similar to that of the fifth embodiment in that a flat lamination of many water absorbing paper layers 12a forms a double-layer structure including an outer layer part 12A and a rear layer part 12B. The folding strip 21 folded between these outer and rear layer parts 12A and 12B forms a space between both layer parts excluding the folded portion. In this manner, a passage space S1 is formed which communicates with the recess 14.

The front side portion of the outer layer part 12A has an absorbent strip 22 accommodated therein and made of a flexible and highly absorbent water insoluble material. One end of the absorbent strip 22 is glued or otherwise secured to the rear face of the folding strip 21, while the other end of the absorbent strip is freely held between the front surface of the outer layer part 12A located above the folding strip 21 and the inner surface of bag element 11. Consequently, the absorbent strip 22 can be taken out of the recess 14 through the opening formed by folding the folding strips. It is desirable to form a deep recess 14 in order to increase the area in which urine can be absorbed. The lamination density and form of the water absorbing paper layers 12a is selected as indicated above.

The napkin thus formed provides the following advantage in practical use in addition to those advantages enumerated above in connection with the second embodiment of the invention. In use, the absorbent strip is taken out of the urine-receiving opening 13 and applied to the underside of the excretory organs. The urine remaining on the body after discharge is wiped off by the absorbent strip 22 rubbing thereagainst when the napkin is removed from the body. Therefore, surrounding lingerie is not stained and any uncomfortableness can be completely eliminated.

Figure 19:
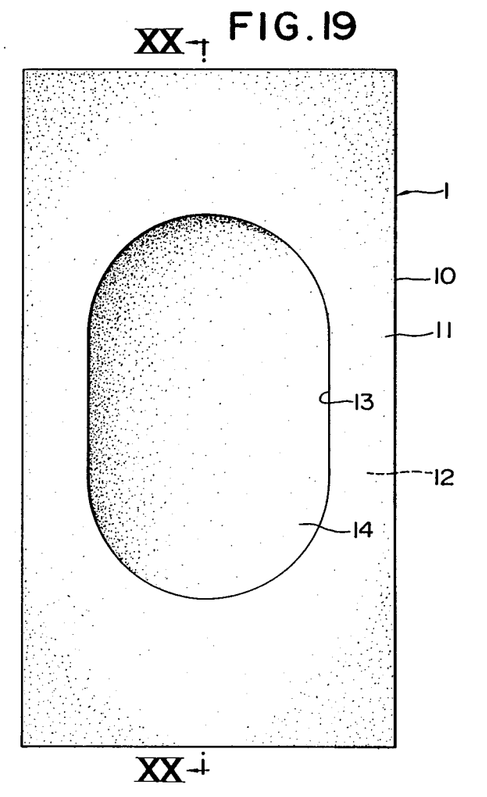
FIGS. 19 and 20 show a napkin for receiving feces in accordance with a seventh embodiment which can be used by males as well as females, FIG. 19 showing a front view of the napkin, and FIG. 20 showing a vertical sectional view taken along line XX—XX of FIG. 19.
Figure 20:
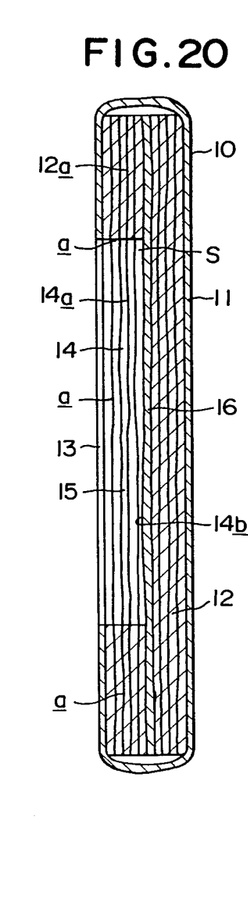

As shown in FIGS. 19 and 20, a napkin 1 for receiving feces in accordance with a seventh embodiment of this invention includes a napkin body 10 including a membranous bag element 11 and an absorbent element 12. The bag element 11 is made of a water-permeable paper material, such as synthetic fiber paper, which is water insoluble and shaped into the form of an elongate bag having flat side surfaces. The front part of the bag element which is to be brought into contact with the excretory organs, that is, the wider surface of the bag element, is provided with an elongate opening 13 and the absorbent element 12 is accommodated within the bag element 11. The bag element may have an elongate rectangular form as shown in FIG. 19, or a reversed trapezoidal or elongate elliptical form, or any other suitable form, when seen from the front side. The napkin body 10 is of a size larger than that of a sanitary napkin or urine-absorbing napkin.

The absorbent element 12 is made as discussed above. It is desirable to form a deep recess 14 in order to ensure a large space in which faeces can be received as well as to increase an area in which loose feces can be absorbed.

The lamination density of the respective water absorbing paper layers 12a is selected as in the first embodiment. Capillaries a open into and communicate with the inner circumferential surface 14a of the recess 14, so that feces, and particularly loose feces, can be absorbed under capillary action not only by the bottom surface 14b, but also by the inner circumferential surface 14a. The napkin 1 can be readily bent in the transverse direction so that it can be securely held on the body and be appropriately deformed. Only the rear surface of the bag element 11 is preferably made of a waterproof film.

The napkin thus formed in accordance with the seventh embodiment provides the following advantages in practical use. Since the bag element 11 forming the outer surface of the napkin 1 is made of water-permeable paper which is water insoluble and agreeable to the touch, the napkin 1 can be comfortably worn.

Since the inner circumferential area corresponding to the depth of the recess 14 serves to absorb loose feces and since the small spaces between the respective water absorbing paper layers 12a laminated in the recess 14 serve as capillaries a which open into and communicate with the inner circumferential surface 14a of the recess, the absorptivity of the paper itself is combined with the absorptivity provided by the respective capillaries to significantly increase the absorptive power of the napkin assembly. Consequently, the napkin can be safely used to receive even the loose feces.

Since the absorbent element 12 is formed of a flat lamination of a number of water-absorbing paper layers 12a, it is excellent in flexibility and can be appropriately deformed. Therefore, it feels soft and smooth when brought into contact with the body. Further, even after the napkin 1 absorbs loose feces, it still remains flexible and soft. In summary, the napkin does not make the user feel uneasy about the foreign matter, that is, the napkin, which is in contact with the body.

Figure 21:
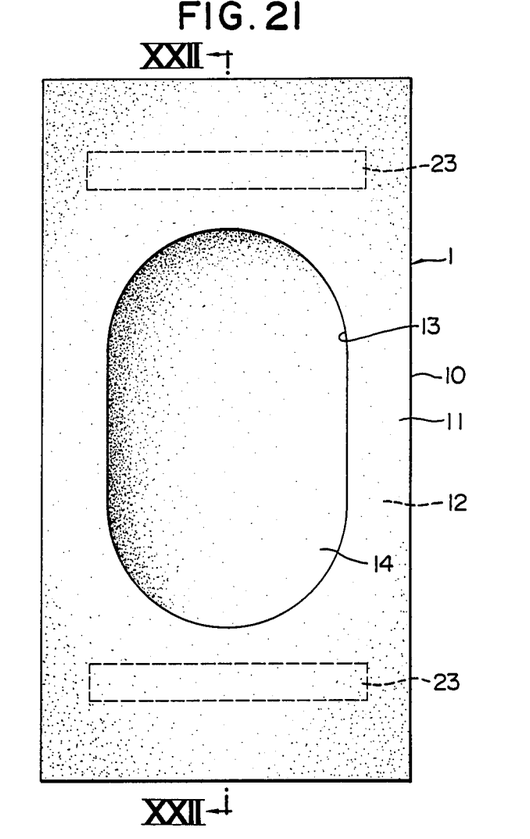
FIGS. 21 and 22 show a napkin for receiving feces in accordance with an eighth embodiment which can be used by males as well as females, FIG. 21 showing a front view of the napkin, and FIG. 22 showing a vertical sectional view taken alone line XXII—XXII of FIG. 21.
Figure 22:
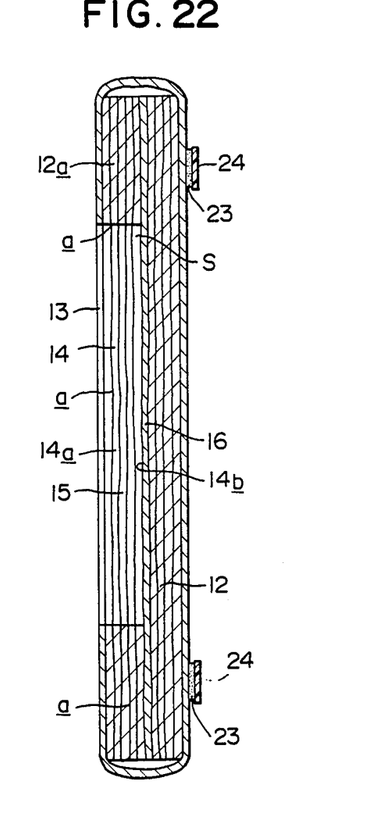

As shown in FIGS. 21 and 22, a napkin 1 for receiving feces in accordance with an eighth embodiment of this invention includes all the features of the seventh embodiment and further includes adhesive portion 23 provided on the rear surface of the bag element 11, and strip-off tapes 24 provided on the adhesive portions 23. The width of the napkin 1 can be reduced to a greater extent so that it can be securely held on the body and appropriately deformed. The adhesive portions 23 may be provided in appropriate positions on the rear surface of the bag element 11 as shown in FIGS. 21 and 22. These adhesive portions 23 are made of a pressure-sensitive adhesive or a two-sided tape. Only the rear surface of the bag element 11 is preferably made of a waterproof film.

The napkin thus formed in accordance with the eighth embodiment provides the following advantages in practical use in addition to those advantages enumerated above in connection with the seventh embodiment. The adhesive portions on the rear surface of the bag element integrally adhere to the user's underwear simply by inserting the napkin between the underwear and the excretory organs. The napkin does not slip off during walking or other usual movements. Consequently, the user's underwear is no longer stained and any uncomfortableness can be completely eliminated. The napkin can be safely used especially to receive loose feces. The feces remaining on the body can be wiped off by the surface of the absorbent element.

The napkin 1 according to the first to seventh embodiments as described above may be modified by providing adhesive portions as in the eighth embodiment on the rear surface of the napkin. Alternatively, the adhesive portions may be provided on the front side of the napkin so as to directly adhere to the skin. In this case, the problem of slippage can be completely avoided so that the napkin is very useful for receiving feces. Furthermore, the bag element 11 may be made of a waterproof film, so that the skin area which is in contact with the surface of the napkin body 10 may not be stained by loose feces. In this case, if the front surface of the bag element made of a waterproof film is covered with a porous paper material or the like which is agreeable to the touch, the space between the napkin and the body will not become stuffy and therefore the napkin can be comfortably worn. Ths also applies to the napkin for absorbing urine in accordance with the second to sixth embodiments.

In the respective embodiments as described above, the recess 14 may be formed such that the width is increased from the inlet toward the bottom of the recess. The recess may have various shapes such as a frustoconical shape or the like. Alternatively, the width of the recess may be stepwise increased from the inlet toward the bottom thereof. As a result, the inner area of the recess which can receive the excretions, i.e., the absorption efficiency, is increased. The napkin thus shaped can rapidly absorb menstrual blood and urine, and is therefore preferably used for such purposes. It can be also effectively used as a napkin for receiving feces, since the feces are more reliably received in the enlarged space and even loose feces can be efficiently absorbed and received.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A sanitary napkin for receiving bodily excretions, said sanitary napkin comprising
    an elongated, flexible, absorbent element having opposite front and rear surfaces which are smooth and elongated, said absorbent element comprising a lamination of a plurality of elongated water-absorbing paper layers which are rimpled in their elongate dimension, some of said elongated water-absorbing paper layers nearest said front surface of said absorbent element including portions which are folded back inwardly of said absorbent element so as to provide an excretion-receiving recess in said absorbent element extending from its front surface towards its rear surface and a generally C-shaped excretion-receiving passage space communicating with said recess, said generally C-shaped passage space having a generally triangular-shaped cross section, the capillaries between said water-absorbing paper layers communicating with said recess and said generally C-shaped passage space, and
    an elongated, waterproof bag element securely surrounding said absorbent element, said bag element having a front surface covering the front surface of said absorbent element and a rear surface covering the rear surface of said absorbent element, the front surface of said bag element including an opening which is in alignment with the recess in the absorbent element therein.

2. A sanitary napkin as defined in claim 1, wherein said recess in said absorbent element is elongated and wherein said opening in said bag element is correspondingly elongated.

3. A sanitary napkin as defined in claim 2, wherein both said recess in said absorbent element and said opening in said bag element are elliptical.

4. A sanitary napkin as defined in claim 1, wherein said recess in said absorbent element is round and wherein said opening in said bag element is round.

5. A sanitary napkin as defined in claim 1, including a water-permeable membrane positioned between said absorbent element and said bag element to cover the recess in said absorbent element.

6. A sanitary napkin as defined in claim 1, wherein said bag element includes at least one adhesive means on the side of the front surface thereof which faces away from the absorbent element.

7. A sanitary napkin as defined in claim 1, wherein said bag element includes at least one adhesive means on the side of the rear surface thereof which faces away from the absorbent element.

8. A sanitary napkin for receiving bodily excretions, said sanitary napkin comprising
    an elongated, flexible, absorbent element having opposite front and rear surfaces which are smooth and elongated, said absorbent element comprising a lamination of a plurality of elongated water-absorbing paper layers which are rimpled in their elongated dimension, some of said elongated water-absorbing paper layers nearest said front surface of said absorbent element including portions which are folded back inwardly of said absorbent element so as to provide an excretion-receiving recess in said absorbent element extending from its front surface towards its rear surface and a generally C-shaped excretion-receiving passage space communicating with said recess, said generally C-shaped passage space having a generally triangular-shaped cross section, the capillaries between said water-absorbing paper layers communicating with said recess and said generally C-shaped passage space,
    an elongated, waterproof bag element securely surrounding said absorbent element, said bag element having a front surface covering the front surface of said absorbent element and a rear surface covering the rear surface of said absorbent element, the front surface of said bag element including an opening which is in alignment with the recess in the absorbent element therein, and
    an absorbent strip having opposite ends, one end of said absorbent strip being attached to the inwardly folded back portions of the water-absorbing paper layers which provide said excretion-receiving recess and said laterally-extending excretion-receiving passage spaces and other end being extendable through said opening in said bag element.

* * * * *